US012376905B2

(12) United States Patent
Gurevich et al.

(10) Patent No.: US 12,376,905 B2
(45) Date of Patent: Aug. 5, 2025

(54) AUGMENTED REALITY DISPLAY OF SURGICAL IMAGING

(71) Applicant: SG Devices, Inc., North Oaks, MN (US)

(72) Inventors: Sergey Gurevich, North Oaks, MN (US); Stephen Alexander George, North Oaks, MN (US)

(73) Assignee: SG Devices, Inc., North Oaks, MN (US)

( * ) Notice: Subject to any disclaimer, the term of this patent is extended or adjusted under 35 U.S.C. 154(b) by 524 days.

(21) Appl. No.: 17/085,653

(22) Filed: Oct. 30, 2020

(65) Prior Publication Data

US 2021/0161596 A1     Jun. 3, 2021

Related U.S. Application Data

(60) Provisional application No. 63/034,724, filed on Jun. 4, 2020, provisional application No. 62/942,521, filed on Dec. 2, 2019.

(51) Int. Cl.
*A61B 34/10*     (2016.01)
*A61B 34/00*     (2016.01)
(Continued)

(52) U.S. Cl.
CPC ............. *A61B 34/10* (2016.02); *A61B 34/20* (2016.02); *A61B 34/25* (2016.02); *A61B 90/37* (2016.02);
(Continued)

(58) Field of Classification Search
CPC ... A61B 34/10; A61B 34/20; A61B 2090/365; A61B 34/25; A61B 90/37; A61B 90/36;
(Continued)

(56) References Cited

U.S. PATENT DOCUMENTS 8,880,153 B2    11/2014   Pfister
10,010,379 B1    7/2018   Gibby et al.
(Continued)

FOREIGN PATENT DOCUMENTS

JP    H08-24227    1/1996
JP    2011-125462    6/2011
(Continued)

OTHER PUBLICATIONS

International Search Report and Written Opinion in International Appln. No. PCT/US2020/058280, dated Jan. 29, 2021, 12 pages.
(Continued)

*Primary Examiner* — Peter Luong
(74) *Attorney, Agent, or Firm* — Fish & Richardson P.C.

(57) ABSTRACT

An imaging sensor includes a radiation sensor. An imaging controller is configured to: (i) generate an imaging-datastream based on the sensed phenomena and (ii) transmit, to a central controller, the imaging-datastream. The central controller is configured to: receive the imaging-datastream; generate, from the imaging-datastream, a high-contrast videostream in which surgical tools and vascular tissue is represented with a dark color and in which surrounding tissue is represented with a light color, the dark color being darker than the light color; and transmit, to an augmented-reality controller, the high-contrast videostream. The augmented-reality controller is configured to: (i) receive the high-contrast videostream and (ii) instruct a head-worn display to render the high-contrast videostream such that the surgical tools and vascular tissue is rendered with the dark color. The head-worn display is configured to render the high-contrast videostream such that the surgical tools and vascular tissue is rendered with the dark color.

20 Claims, 15 Drawing Sheets

(51) Int. Cl.
*A61B 34/20* (2016.01)
*A61B 90/00* (2016.01)

(52) U.S. Cl.
CPC ... *A61B 2034/102* (2016.02); *A61B 2034/105* (2016.02); *A61B 2034/2065* (2016.02); *A61B 2090/365* (2016.02); *A61B 2090/376* (2016.02)

(58) Field of Classification Search
CPC ........ A61B 2034/102; A61B 2034/105; A61B 2034/2065; A61B 2034/2048; A61B 2090/376; A61B 2090/3612; A61B 2090/372; A61B 2090/3762; A61B 2090/502; A61B 2017/00207; G06N 3/045; G06N 3/08
See application file for complete search history.

(56) References Cited

U.S. PATENT DOCUMENTS

| | | | | |
|---|---|---|---|---|
| 11,250,600 | B2 * | 2/2022 | Ye | G06T 11/008 |
| 2002/0162154 | A1 * | 11/2002 | Shamam | A41D 13/1245 2/69 |
| 2007/0174947 | A1 | 8/2007 | Schneider | |
| 2009/0003511 | A1 * | 1/2009 | Roy | A61B 5/415 378/4 |
| 2009/0192385 | A1 | 7/2009 | Meissner et al. | |
| 2010/0256558 | A1 | 10/2010 | Olson et al. | |
| 2012/0238871 | A1 | 9/2012 | Pfister | |
| 2012/0257809 | A1 * | 10/2012 | Miyamoto | G06T 5/50 382/132 |
| 2016/0157802 | A1 | 6/2016 | Anderson | |
| 2017/0219704 | A1 * | 8/2017 | Call | G01S 15/89 |
| 2018/0074332 | A1 * | 3/2018 | Li | G06F 3/012 |
| 2018/0092698 | A1 | 4/2018 | Chopra et al. | |
| 2018/0303446 | A1 | 10/2018 | Schweizer | |
| 2018/0344266 | A1 * | 12/2018 | Altmann | A61B 6/487 |
| 2019/0239973 | A9 * | 8/2019 | Esterberg | A61B 34/20 |
| 2019/0318476 | A1 * | 10/2019 | Isgum | G06N 20/00 |
| 2020/0183171 | A1 * | 6/2020 | Robaina | G06F 3/013 |
| 2021/0045813 | A1 * | 2/2021 | Wickham | A61B 34/20 |
| 2021/0386480 | A1 * | 12/2021 | Tolkowsky | A61B 34/20 |

FOREIGN PATENT DOCUMENTS

| | | |
|---|---|---|
| JP | 2012213544 A * | 11/2012 |
| WO | WO 2011074657 | 6/2011 |

OTHER PUBLICATIONS

International Preliminary Report on Patentability in International Appln. No. PCT/US2020/058280, dated Jun. 16, 2022, 10 pages.
Extended European Search Report in European Appln. No. 20895847.0, dated Mar. 2, 2023, 10 pages.
Hernandez-Vela et al., "Accurate Coronary Centerline Extraction, Caliber Estimation, and Catheter Detection in Angiographies," IEEE Transactions on Information Technology in Biomedicine, Nov. 2012, 16(6):1332-1340.

* cited by examiner

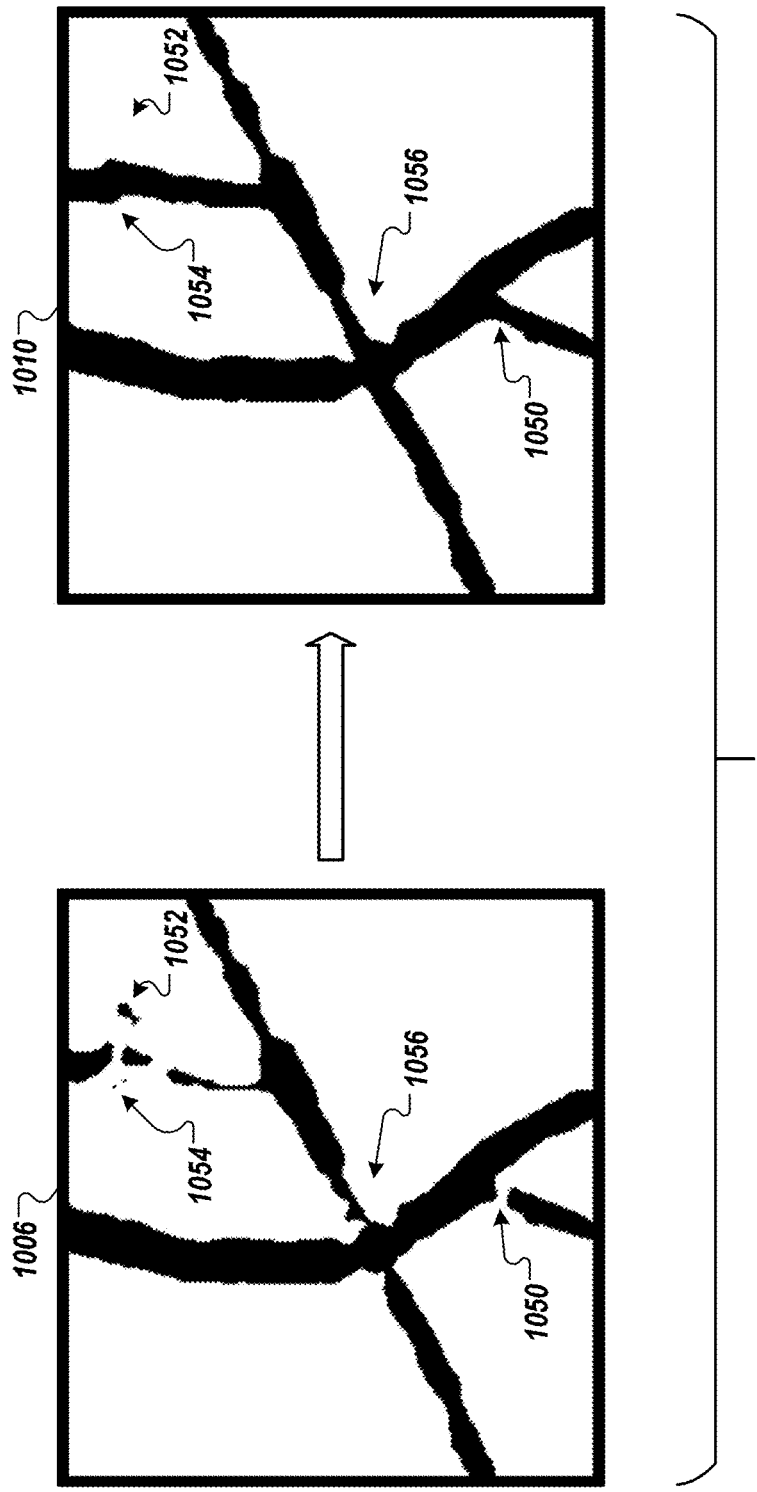

AUGMENTED REALITY DISPLAY OF SURGICAL IMAGING

CROSS-REFERENCE TO RELATED APPLICATIONS

This application claims the benefit of U.S. Provisional Application Ser. No. 63/034,724, filed Jun. 4, 2020, and U.S. Provisional Application Ser. No. 62/942,521, filed Dec. 2, 2019. The disclosures of the prior applications are considered part of (and are incorporated by reference in) the disclosure of this application.

TECHNICAL FIELD

This document describes technology related to augmented reality displays that are usable in sterile operating environments by medical clinicians.

BACKGROUND

Fluoroscopy is an imaging technique that uses X-rays to obtain real-time moving images of the interior of an object. In its primary application of medical imaging, a fluoroscope allows a physician to see the internal structure and function of a patient, so that the pumping action of the heart or the motion of swallowing, for example, can be observed on the screen of a display.

Augmented reality (AR) is an interactive experience of a real-world environment where the objects that reside in the real world are enhanced by computer-generated perceptual information, sometimes across multiple sensory modalities, including visual, auditory, haptic, somatosensory and olfactory. AR can be defined as a system that fulfills three basic features: a combination of real and virtual worlds, real-time interaction, and accurate 3D registration of virtual and real objects. The overlaid sensory information can be constructive (i.e., additive to the natural environment), or destructive (i.e., masking of the natural environment).

SUMMARY

In one implementation a system includes an imaging sensor includes a radiation sensor, the imaging sensor configured to sense a phenomena in a patient's body based on a reception of radiation that has passed through the patient's body. The system includes an imaging controller comprising a processor and memory, the imaging controller configured to: (i) generate an imaging-datastream based on the sensed phenomena and (ii) transmit, to a central controller, the imaging-datastream. The system includes the central controller comprising a processor and memory, the central controller configured to: receive the imaging-datastream; generate, from the imaging-datastream, a high-contrast videostream in which surgical tools and vascular tissue is represented with a dark color and in which surrounding tissue is represented with a light color, the dark color being darker than the light color; and transmit, to an augmented-reality controller, the high-contrast videostream. The system includes the augmented-reality controller comprising a processor and memory, the augmented-reality controller configured to: (i) receive the high-contrast videostream and (ii) instruct a head-worn display to render the high-contrast videostream such that the surgical tools and vascular tissue is rendered with the dark color. The system includes the head-worn display comprising a transparent view-area and a renderer configured to render onto the view-area, the head-worn display configured to render the high-contrast videostream such that the surgical tools and vascular tissue is rendered with the dark color. Other implementations include systems, devices, methods, computer-readable memory, and software.

Implementations can include one or more of the following features. To generate, from the imaging-datastream, a high-contrast videostream in which surgical tools and vascular tissue is represented with a dark color, the controller is further configured to generate, from the imaging-datastream, a full-scale videostream in which surgical tools and vascular tissue have a first contrast with surrounding tissue; and generate, from the full-scale videostream, the high-contrast videostream such that in the high-contrast videostream, surgical tools and vascular tissue have a second contrast with surrounding tissue, the second contrast being greater than the first contrast. To generate, from the full-scale videostream, the high-contrast videostream, the controller is further configured to increase the contrast of the full-scale videostream such that the high-contrast videostream contains only the dark color and the light color. To generate, from the full-scale videostream, the high-contrast videostream, the controller is further configured to invert the colors of the full-scale videostream. The augmented-reality controller is communicably coupled to the head-worn display by at least a data cable. The system further comprising a sterile gown having a port through which the data cable can pass, resulting in the augmented-reality controller being wearable by a wearer in a sterile environment and the augmented-reality controller being wearable by the wearer in a non-sterile environment. The head-worn display comprises radiation shielding positioned to protect a wearer from radiation. The central controller is further configured to determine a measure of blockage of an area of vascular tissue.

Implementations can provide some, all, or none of the following advantages. In accordance with the innovations described herein, an AR display of medical imaging can be provided to a clinician, allowing the clinician to move about while maintaining a view of the medical imaging. This can facilitate more flexibility and comfort while performing a procedure that uses medical imaging. In addition, by displaying surgical tools and tissue of interest in black, with other tissue displayed in white, the images can be provided with high contrast that is still legible even when the AR display is pointed to a light source, is used in a well-lit room, etc. The described technology can provide a user with improved ergonomics. The ability to move with a wireless AR display allows the user to be untethered from the monitor and allows them to increase the distance between themselves and an x-ray source, improving user safety. In many cases, a significant amount of radiation exposure to the eyes is from scatter coming from underneath glasses as a result of looking away from the radiation source and towards a monitor. Having an AR display can allow optimal head positioning to shield against radiation exposure. Lead shielding of the AR display can allow increased radiation protection to the head, brain, eyes. This technology can also increase space saving in an operating room by eliminating the need for large, multiple monitors that can take up a space. High contrast ratio in images can improve visualization of grayscale views in augmented reality. This technology can allow for remote viewing and remote procedure and can allow for the switching between multiple imaging modalities simultaneously, fluoroscopy, ultrasound, reference CT, IVUS, hemodynamic analysis, iFR, MacLab, chart review, etc. This technology may also improve sizing of the vascular tissue due to better edge definition.

DESCRIPTION OF DRAWINGS

FIG. 10B shows an example of a raw image and a noise/artifact free or reduced image.

Like reference symbols in the various drawings indicate like elements

DETAILED DESCRIPTION

In accordance with some embodiments described herein, an augmented reality display can be used to show medical imaging. To ensure that the wearer can perceive the image, the image may be processed to have a high contrast between elements of interest (e.g., vascular tissue, surgical tools, etc.) and areas of low interest (e.g., non-vascular tissue, etc.). For example, elements of interest may be rendered in a black color and other elements may be rendered in a white color, resulting in high-contrast rendering that is observable even when the augmented reality display (e.g., a head-worn display) is pointed at a light source.

Figure 1A:
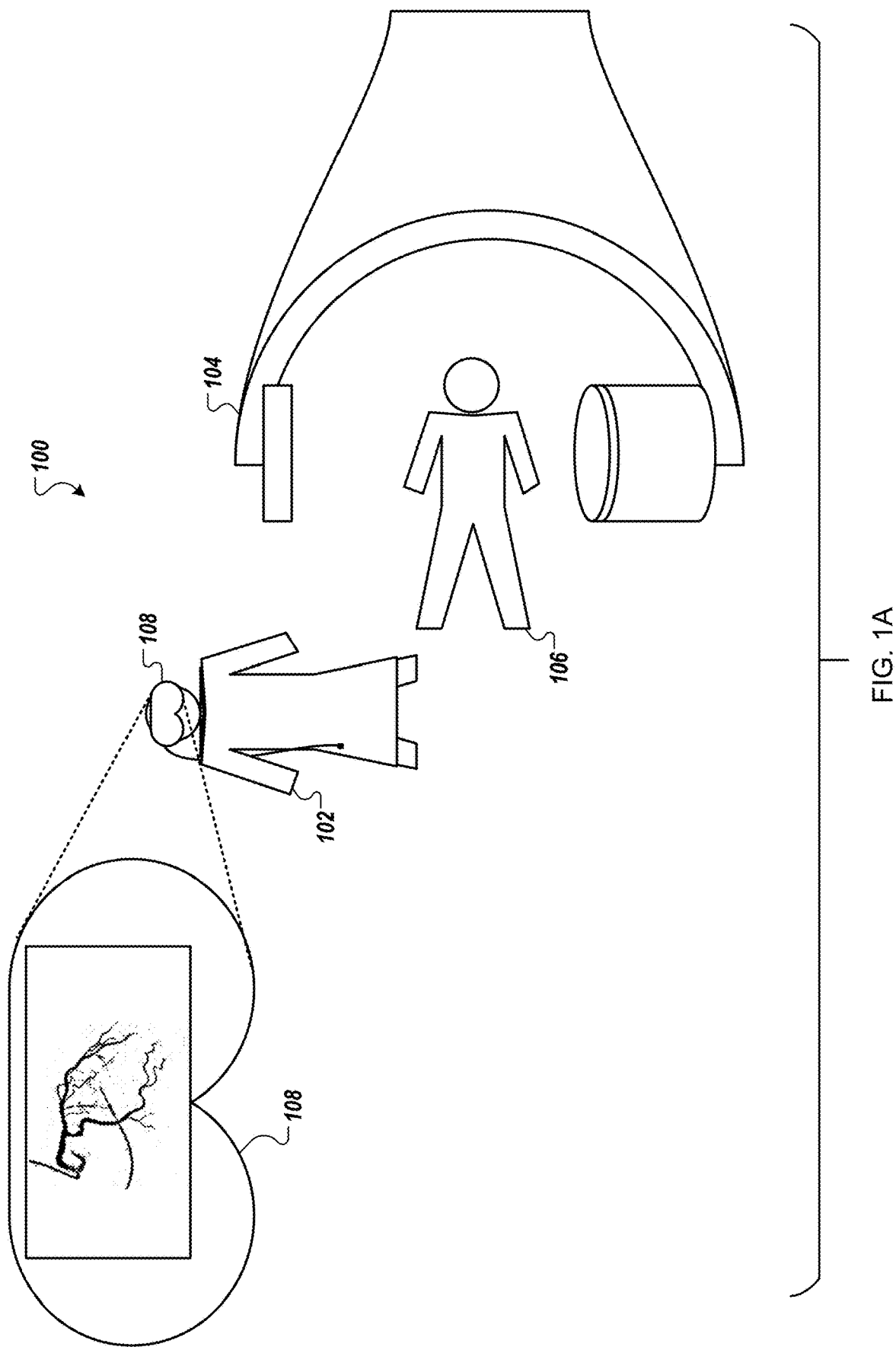
FIG. 1A shows a diagram of an example system for providing an augmented reality display of surgical imaging.

FIG. 1A shows a diagram of an example system 100 for providing an augmented reality display of surgical imaging. In the system 100, a clinician 102 (e.g., a surgeon, interventionalist, etc.) is using a medical imager 104 (e.g., a fluoroscope) to image a patient 106 while performing a procedure on the patient 106. In this example, the clinician 102 is performing a catheterization on the patient 106, and features of such a procedure will be used for the purposes of explanation in this document.

However, the technology described can be used for many other purposes. For example, the clinician 102 may be a speech pathologist performing a modified barium swallow study to diagnose oral and pharyngeal swallowing dysfunction. In another example, the clinician 102 may be a veterinarian performing a procedure on a non-human animal patient. In another example, the clinician 102 may be a researcher monitoring a non-therapeutic experiment. In another example, the system 100 can be used outside of a medical setting. For example, the system 100 may be used by a manufacturing parts inspector that is subjecting a manufactured part to radiographic or ultrasonic inspection to ensure that a manufacturing process was undertaken correctly. In some cases, the welding of two metal pieces can benefit from such inspection, because voids in the weld, which can weaken the weld, may not be visible from the surface.

In some examples, the medical imager 104 may be a different type of imager than a fluoroscope. For example, the medical imager 104 may be a computed tomography scanner, a positron-emission tomographic, or the like. In any case, the medical imager 104 can generate images based on one or more phenomenon in the patient's 106 body and generate image(s) or video of the phenomena.

The image(s) or video can be processed for ease of viewing on an augmented-reality display 108 worn by the clinician 102. For example, the image(s) or video may be processed into a monochromatic image or video and rendered onto a view-screen of the augmented-reality display 108.

Figure 1B:
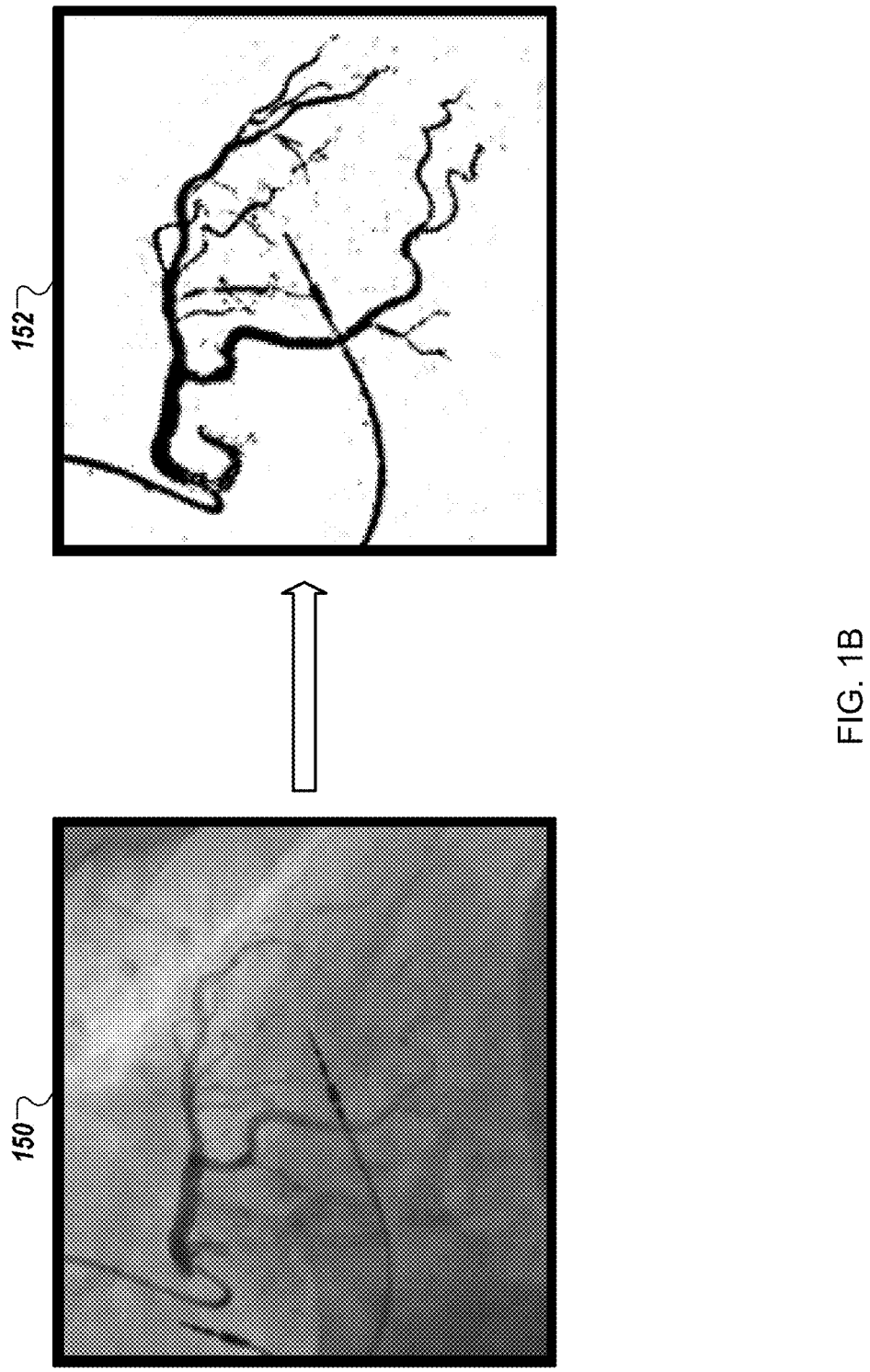
FIG. 1B shows a modification of an image in preparation for use in an augmented reality display.

FIG. 1B shows a modification of an image in preparation for use in an augmented reality display. Image 150 is a greyscale image created by the medical imager 104, and image 152 is a modified image that has been created from the image 150 and presented in the augmented reality display 108

Figure 2:
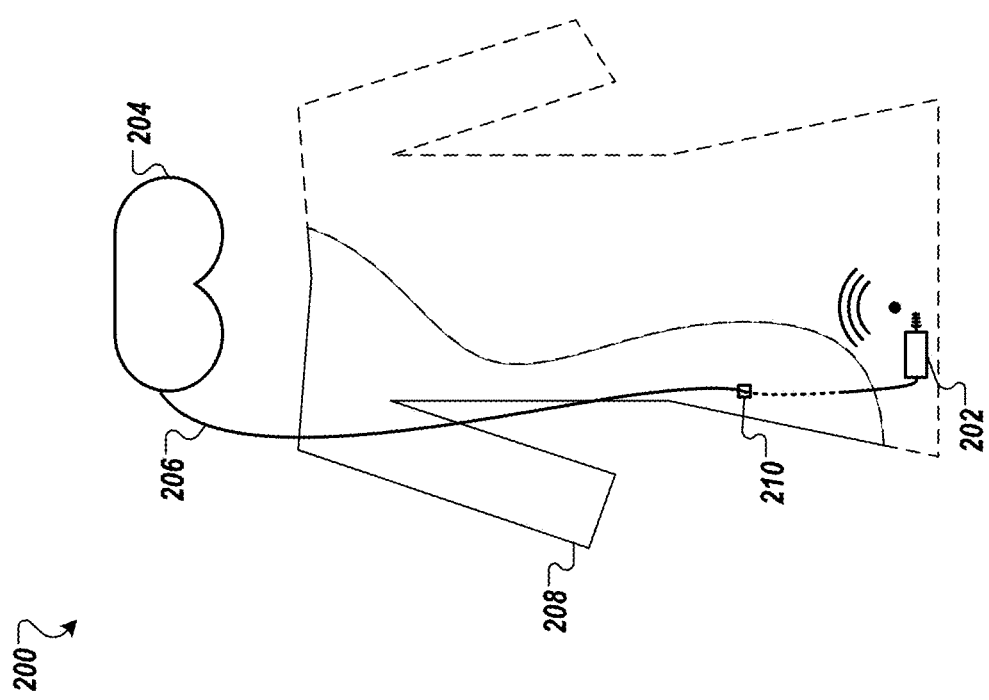
FIG. 2 shows a diagram of example hardware that can be used for providing an augmented reality display of surgical imaging.

FIG. 2 shows a diagram of example hardware 200 that can be used for providing an augmented reality display of surgical imaging. For example, the hardware 200 can be used by the clinician 102 (FIG. 1) while operating in a sterile operating theater.

The hardware 200 includes an augmented-reality controller 202 that is communicably coupled to a head-worn display 204 (e.g., coupled wirelessly or by a data cable 206 as shown). In some embodiments, the head-worn display 204 can be shaped to be worn as a pair of glasses or a visor over a human user's eyes and/or face. The head-worn display 204 can include a view-area to transmit to the user a view of the environment actually in front of the user's face. This view-area may be or include a clear area made of materials such as plastic, glass, lead glass, and the like. In such a case, light reflected by physical objects can pass through the view-area into the user's eye for perception. In some configurations, the view-area may be or include a computer-display and a camera mounted on the head-worn display. In such a case, the display area may be normally opaque, and when powered on the camera may capture live, color video of the environment in front of the head-worn display 204 and render this live, color video of the environment on the view-area.

In addition, in some embodiments the head-worn display 204 can render a videostream on the view-area. For example, one or more video projectors can project the videostream onto the view-area, from where it is reflected and enters the user's eyes. In another example, the view-area may include a computer-display that superimposes the videostream over top of the live, color video of the environment.

In some cases, the head-worn display 204 comprises radiation shielding positioned to protect a wearer from radiation (e.g., protect the eyes, protect the head). For example, when used in an environment with otherwise potentially dangerous amounts of radiation, the physical structure of the head-worn display 204 may shield the wearer's eyes from the radiation. One such example is an operating room with a running fluoroscope. That is, when the head-worn display 204 is used by a wearer to see the imaging provided by a fluoroscope, the head-worn display 204 may both show the imaging provided by the fluoroscope and simultaneously protect the wearer's eyes from the radiation from the fluoroscope.

In some cases, the head-worn display 204 includes a view-area that is clear and has a lens that is made of or includes a layer of lead glass. As a clear material, the lead glass may allow the user to see the actual environment, and may reflect a projected videostream back to the user, providing an augmented reality experience. Further, as a ray-shielding material, the lead glass may prevent radiation from passing through the lens into the wearer's eyes. In some cases, other photo-translucent, radiopaque materials can be used, including but not limited to lead barium glass (e.g. 55% PbO lead oxide), lead acrylic, and boron nitrogen nanotube composite glass. In addition, the frame of the head-worn display 204 can also be shielded to provide protection to the user's head, eyes, etc.

The augmented-reality controller 202 can execute computer instructions in order to send a videostream to the head-worn display 204. The augmented-reality controller 202 can also include a battery pack, a wireless antenna, fixed or removable computer memory, and processors. Accordingly, the augmented-reality controller 202 can be worn or otherwise coupled to the user so that the user can conveniently move around without the encumbrance of tether-like cables and the like.

The data cable 206 communicably couples the augmented-reality controller 202 and the head-worn display 204. The data cable 206 can include one or more wires that all for data transmission in one or both directions, and can further include a sheathing to protect the wires, structural components to stiffen and protect the data cable 206, etc.

A sterile gown 208 (shown here in cut-away) can be worn by the wearer of the hardware 200. As will be understood, the sterile gown 208 can be used to create a barrier between the wearer and the sterile theater so that an operation can be performed on a patient while reducing the chance of infection or other adverse event. In some embodiments, the head-worn display 204 and data cable 206 can be sterilized and worn in the sterile theater, while the augmented-reality controller 202 can be worn by the wearer underneath the sterile gown 208 without having to be sterilized.

In some embodiments, the sterile gown 208 can include a port 210 through which the data cable 206 can pass, resulting in the augmented-reality controller 202 being wearable by a wearer in a sterile environment, and resulting in the augmented-reality controller 202 being wearable by the wearer in a non-sterile environment. The port 210 in the sterile gown 208 can allow passage of the data cable 206 from under the sterile gown 208. The port 210 can include overlapping material, adhesive material, etc., to ensure that only the data cable 206 can pass through the port 210 without allowing contaminates to enter the sterile theater.

Figure 3:
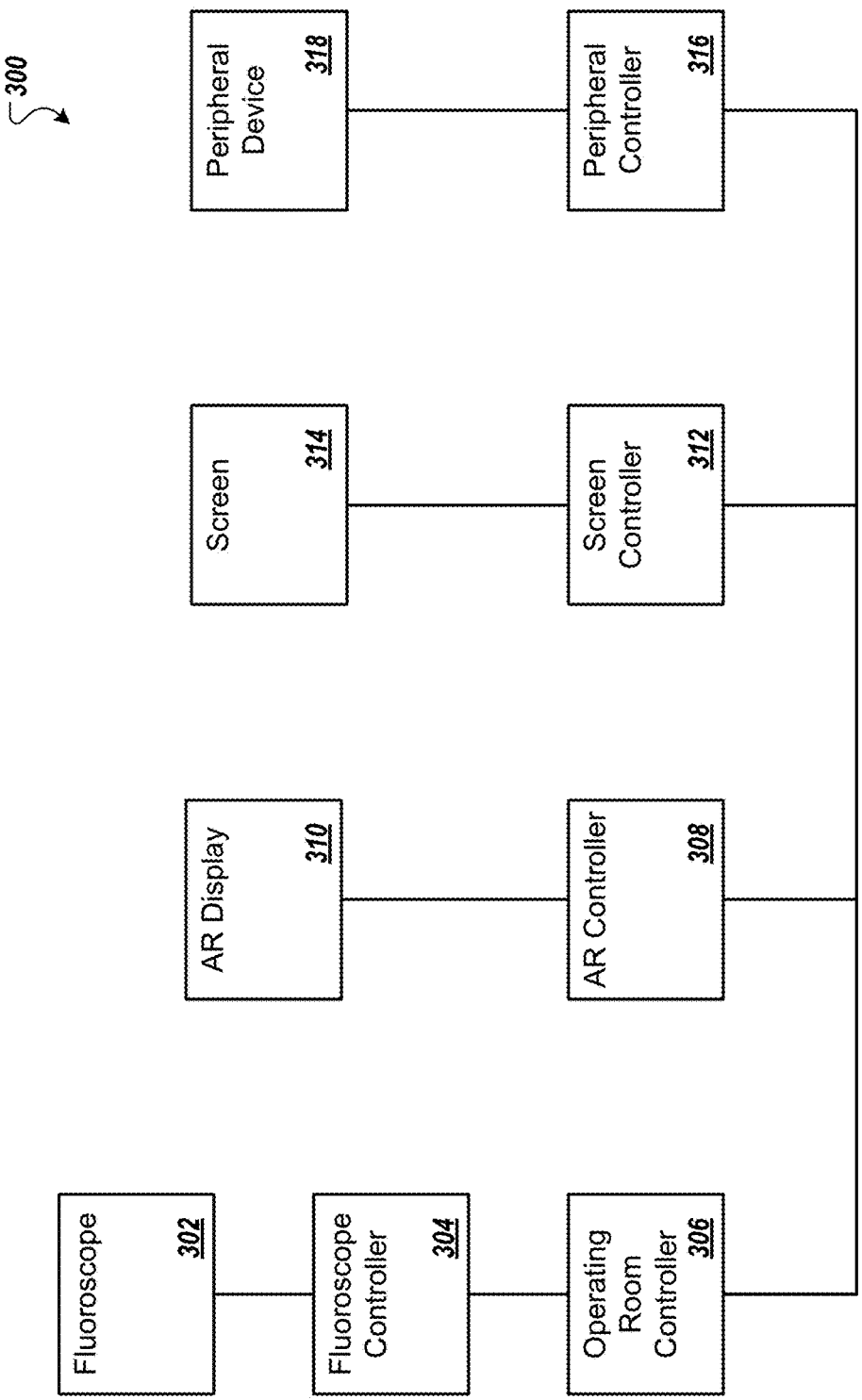
FIG. 3 shows a diagram of an example computing system that can be used for providing an augmented reality display of surgical imaging.

FIG. 3 shows a diagram of an example computing system 300 that can be used for providing an augmented reality display of surgical imaging. This diagram shows some computing components that can work together to generate, transfer, and process data. As will be understood, an operating room can make use of these components as well as other computational and non-computational components. Each of the components can include some or all of the computing hardware described in other portions of this document, including but not limited to hardware processors and computer memory.

Communicable couplings between the elements of the system 300 are shown, though other arrangements are possible. These couplings can include wired and wireless network data connections including, but not limited to, Wi-Fi, BLUETOOTH, and Ethernet data connections.

A fluoroscope 302 and/or other imaging sensors can sense phenomena in the environment (e.g., a patient's body, surgical tools being used, etc.) The fluoroscope 302 can include an energy source that generates radiation and can include a sensor that senses the generated radiation. By placing the body of a patient between the energy source and the sensor, the patient's body can alter the radiation, and this alteration can be used as the basis of imaging of the patient.

The fluoroscope 302 is coupled to a fluoroscope controller 304. The fluoroscope controller 304 can sense phenomena in a patient's body based on a reception of radiation that has passed through the patient's body. For example, the sensor of the fluoroscope 302 may translate the received radiation into electrical signals, and the fluoroscope controller 304 can translate those electrical signals into network data packets.

An operating room controller 306 can be communicably coupled to the fluoroscope controller 304 and other controllers such as an augmented reality controller 308 (e.g., such as the augmented-reality controller 202), a screen controller 312, and one or more peripheral controllers 316. The operating room controller 306 can receive sensor readings from these various controllers and transmit instructions to these various controllers. For example, the operating room controller 306 can execute software that includes an instruction to begin gathering imaging from the fluoroscope 302. The operating room controller 306 can send an instruction to begin recording to the fluoroscope controller 304, and the fluoroscope controller 304 can send messages to the fluoroscope 302 to energize the radiation source and capture sensor data.

An augmented-reality display 310 (e.g., such as the head-worn display 204) can be communicably coupled to the augmented reality controller 308 and include a transparent view-area and a renderer configured to render onto the view-area.

A screen controller 312 can control a screen 314. For example, a liquid crystal display (LCD) monitor may be mounted to the wall in an operating room to act as the screen 314, and the screen controller 312 may receive instructions from the operating room controller 306 to display a graphical user interface (GUI) on the screen 314. This GUI may include vital information about the patient, a clock, or other information of use to the clinicians working in the operating room. In some cases, the screen controller may instruct the screen 314 to display a full-scale videostream or a high-contrast videostream. In some implementations, the augmented reality controller 308 may instruct the augmented reality display to render the high-contrast videostream at the same time as the screen controller 312 instructs the screen 314 to display a full-scale videostream and/or a high-contrast videostream.

Other peripheral devices 318 can also be controlled by corresponding peripheral controllers 316. For example, lighting, heaters, air and fluid pumps, etc. can be operated as peripheral devices 318 controlled by a peripheral controller.

Figure 4:
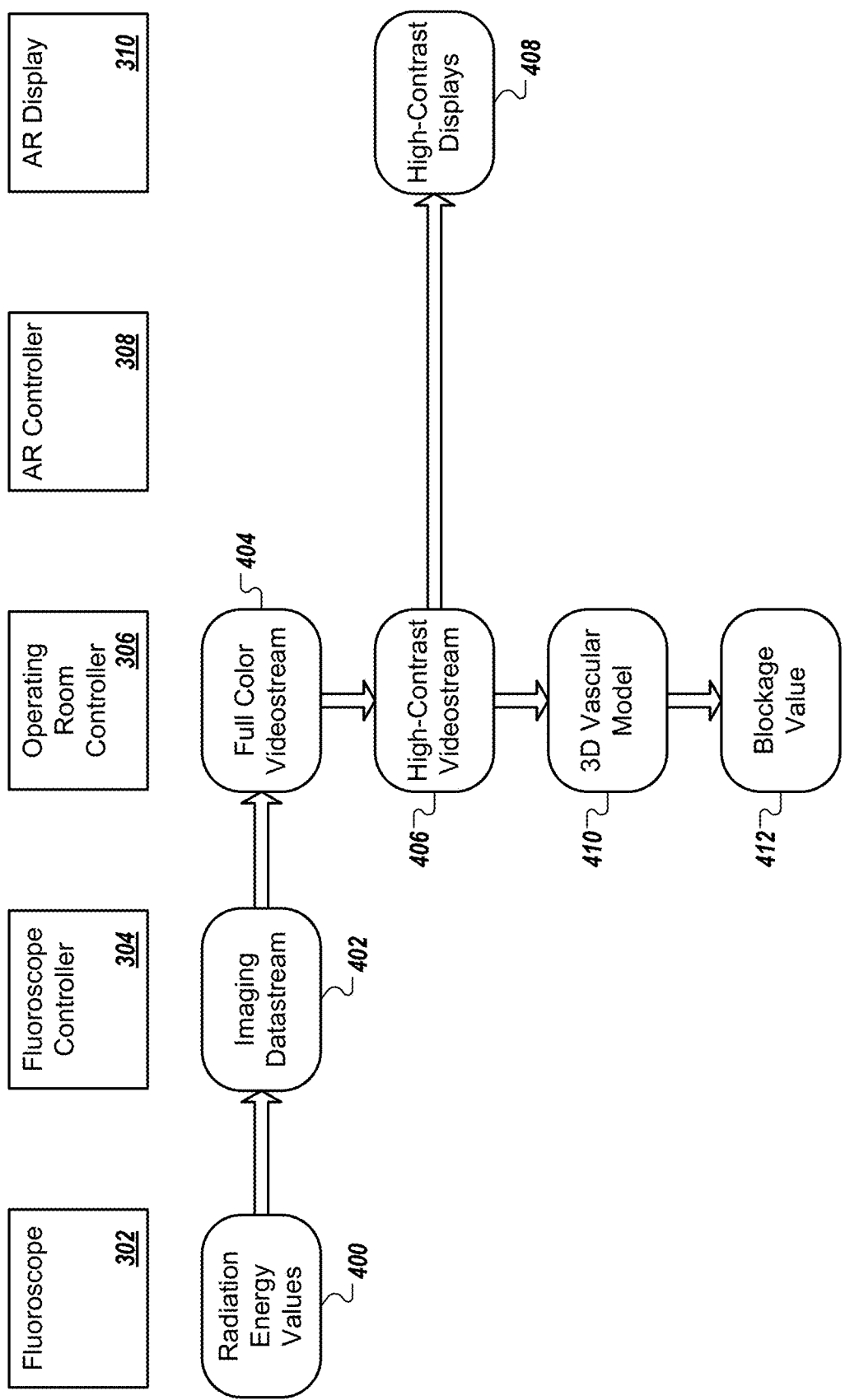
FIG. 4 shows a diagram of example data that can be used for providing an augmented reality display of surgical imaging.

FIG. 4 shows a diagram of example data that can be used for providing an augmented reality display of surgical imaging. As will be understood, the data can be generated, used, transmitted, and received by elements of the system 300 or other systems. As such, the elements of the system 300 will be used to describe the data.

The fluoroscope 302 creates radiation energy values 400. For example, the fluoroscope 302 is configured to sense phenomena in a patient's body based on a reception of radiation that has passed through the patient's body. This radiation is converted into digital or analog signals for the radiation energy values 400, which are then provided to the fluoroscopic controller 304.

The fluoroscopic controller 304 generates an imaging-datastream based on the sensed phenomena. For example, as the radiation energy values 400 are received, the fluoroscopic controller 304 normalizes, packetizes, and marshals them into the imaging datastream 402. The fluoroscopic controller 304 is configured to transmit, to a central controller, the imaging-datastream 402.

The operating room controller 306 is configured to receive the imaging datastream 402. From the imaging datastream 402, the operating room controller 306 is configured to generate, from the imaging datastream 402, a high-contrast videostream 406 in which surgical tools and vascular tissue is represented with a dark color and in which surrounding tissue is represented with a light color, the dark color being darker than the light color. For example, the surgical tools and vascular tissue can be represented with black, and the other tissue can be represented with white. The operating room controller 306 can transmit, to the augmented-reality controller 308, the high-contrast videostream. An example process for generating the high-contrast videostream is described later in this document.

The augmented-reality controller 308 can receive the high-contrast videostream and instruct a head-worn display to render the high-contrast videostream such that the surgical tools and vascular tissue is displayed 408 with the dark color. The head-worn display 310 can render the high-contrast videostream such that the surgical tools and vascular tissue is rendered with the dark color.

Figure 5:
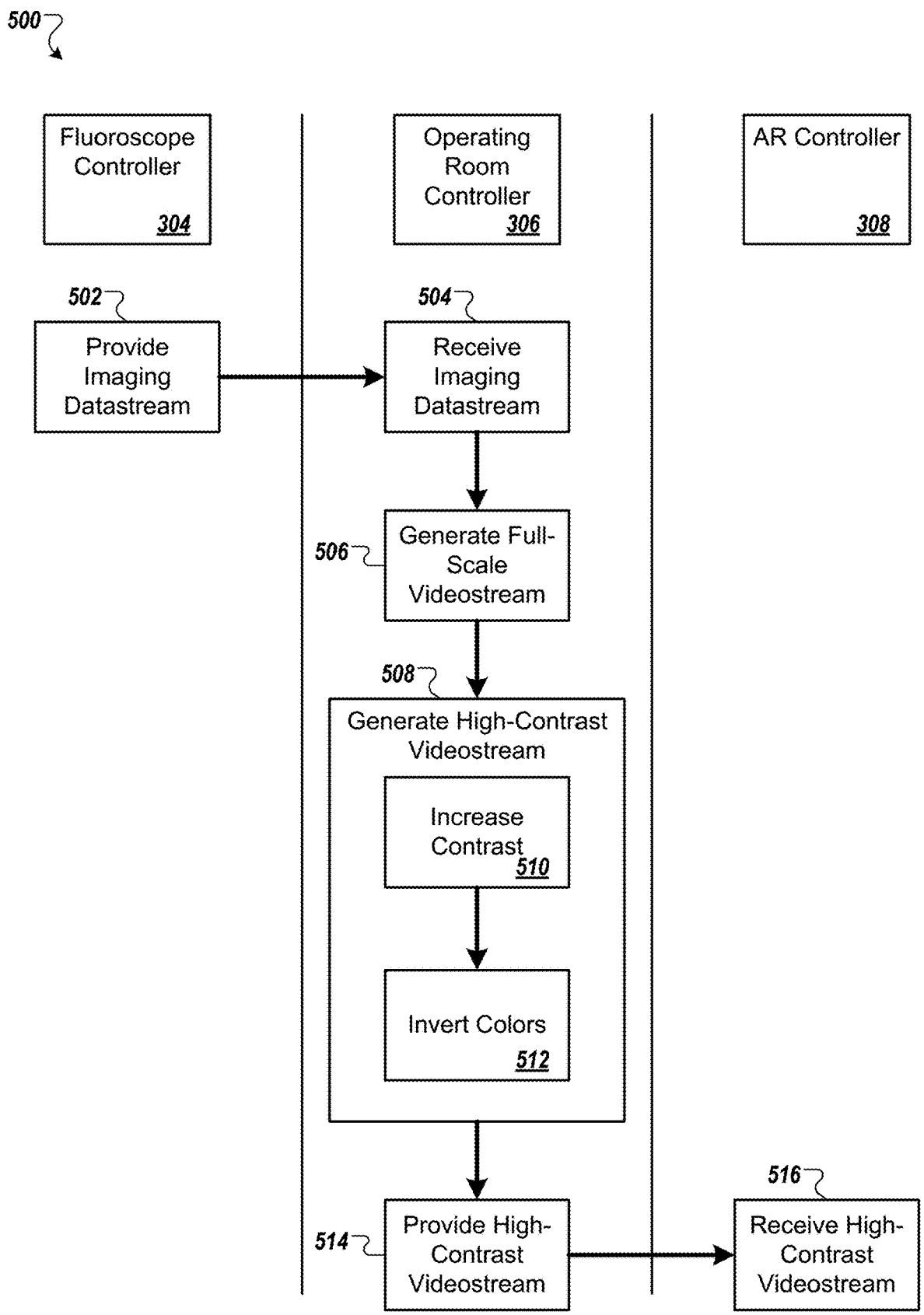
FIG. 5 shows a swimlane diagram of an example process that can be used for providing an augmented reality display of surgical imaging.

FIG. 5 shows a swimlane diagram of an example process 500 that can be used for providing an augmented reality display of surgical imaging. In some cases, the process 500 can be used with the data 400, including in the creation of the high-contrast videostream 406. As such, the system 300 and the data 400 will be used to describe the process 500.

The fluoroscope controller 304 provides the imaging datastream 502 and the operating room controller 306 receives the imaging datastream 504. For example, the fluoroscope controller 304 can provide an ongoing stream of data across an Ethernet connection to the operating room controller 306.

The operating room controller 306 can generate a full-scale videostream from the datastream 506. For example, the imaging datastream 504 can be organized into a 2-dimensional grid that corresponds with a surface of a sensor. Each cell of the grid may store one or more numerical values. The operating room controller 306 can create a videostream with the same number of cells. For each value in the imaging datastream, the operating room controller 306 can create a color value. This color value may be a Red-Green-Blue (RGB) color, a greyscale color (e.g., in which each pixel value is a real number from 0 to 1, inclusive), or other representation.

The operating room controller 306 can generate, from the full-scale videostream, the high-contrast videostream 508.

For example, the high-contrast videostream may be a monochromatic datastream in which each pixel value may contain only the integer value 1 or the integer value 0 to represent black or white. In such a datastream, a tissue of interest (e.g., vascular tissue) and surgical tools may be represented with black and all other tissue may be represented with which. As such, the contrast in the high-contrast videostream is higher than the contrast in the full-scale videostream.

In order to generate the high-contrast videostream, the operating room controller 306 can increase the contrast of the full-scale videostream such that the high-contrast videostream contains only the dark color and the light color 306. For example, if the full-scale videostream has pixel values represented by real numbers from 0 to 1, inclusive, the operating room controller 306 may receive a threshold value. Then, each cell's pixel value is compared to that threshold value. Pixel values greater than the threshold value may be edited to be 1, while pixel values less than the threshold value may be edits to 0. In this way, a monochromatic videostream can be created.

In order to generate the high-contrast videostream, the operating room controller 306 may need to invert the colors of the full-scale videostream 512. For example, in some cases, vascular tissue and/or tools may be represented in the full-scale videostream in a white color. In such a case, the cells edited to have a value of 1 may have their value changed to a 0, and the cells that began with a value of 0 may have their value changed to a 1. In doing so, the black portions of the high-contrast videostream would correspond to light colors in the full-scale video stream, while white portions of the high-contrast videostream would correspond to dark colors in the full-scale video stream. This step may be desirable in cases in which surgical tools and areas of interest are shown in light colors in full-scale videostreams, and may be unneeded in cases in which surgical tools and areas of interest are shown in dark colors in full-scale videostreams.

Further clarifications to the high-contrast videostream can be made. For example, background noise can be reduced by using machine-learning algorithms to subtract background noise in a video with motion. In an example, machine-learning algorithms can be used to darken and lighten individual pixels based on surrounding pixel values. Further details about this machine learning process will be discussed below.

The operating room controller 306 provides the high-contrast videostream 514 and the augmented-reality controller 308 can receive the high-contrast videostream 516. In addition or in the alternative, the high-contrast videostream and/or the full-scale videostream can be sent to one or more other controllers (e.g., the screen controller 312).

Figure 6:
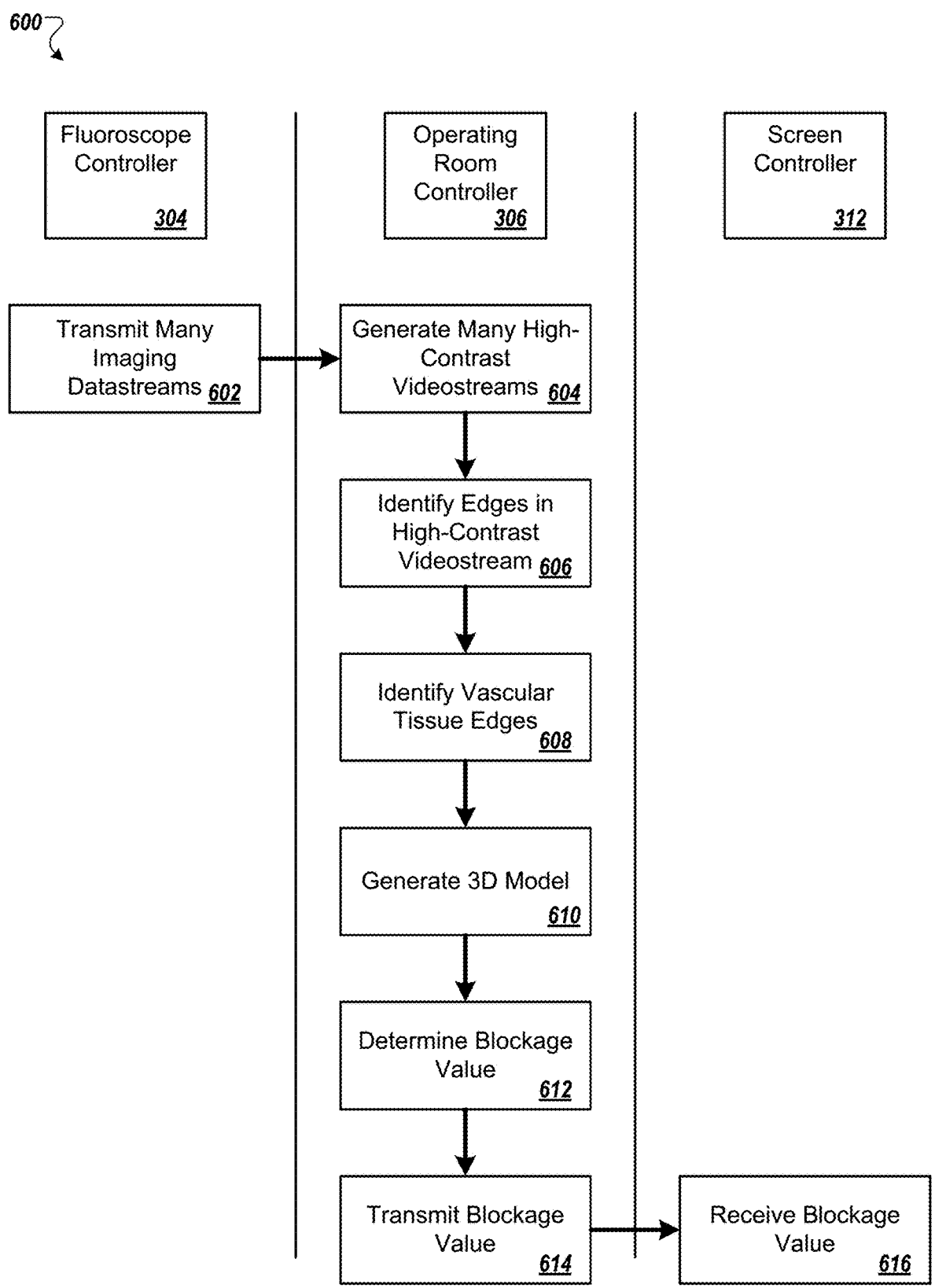
FIG. 6 shows a swimlane diagram of an example process that can be used for determining a blockage of vascular tissue.

In various cases, the high-contrast videostream may be used for image recognition tasks. In some cases, the high-contrast videostream may be examined alone, and in some cases, the high-contrast videostream can be examined in conjunction with the full-scale videostream. FIG. 6 shows a swimlane diagram of an example process 600 that can be used for determining a blockage of vascular tissue. This example process examines the high-contrast videostream in order to enable the operating room controller 306 to determine a measure of blockage of an area of vascular tissue.

The fluoroscope controller 304 transmits many imaging datastreams 602. For example, the fluoroscope controller 304 can collect imaging datastreams from various orientations of a fluoroscope. This can allow for the creation of imaging datastreams of a particular section of vascular tissue from various points-of-view. The operating room controller 306 can generate many high-contrast videostreams 604. For example, from each of the imaging datastreams, the operating room controller 306 can create a corresponding high-contrast videostream. Each of these high-contrast videostreams can show the same vascular tissue a different points-of-view.

The operating room controller 306 can identify vascular tissue edges 608. For example, the operating room controller 306 can subject frames of each of the videostreams to an edge-finding algorithm that draws a 2D line along the interface between high contrast and low contrast areas in an image. As the high-contrast videostreams show vascular tissue in black and other tissue in which, such a line describes the outline of the vascular tissue.

The operating room controller 306 can generate a three-dimensional (3D) model 610. Using the 2D lines from various points-of-view of the vascular tissue, the operating room controller 306 can assemble a 3D model. For example, 3D modeling software can use the angle offset of each line along with the shape of the line as inputs. These inputs are used as constrains in a 3D model generation algorithm that generates a 3D model subject to those constraints. This 3D model thus reflects the shape of the patient's vascular tissue.

The operating room controller 306 determines a blockage value 612. Using the 3D model, the operating room controller 306 can compare the diameter of the vascular tissue at various cross-sections and identify a blockage where the cross-sectional area is reduced. This blockage can then be quantified with a blockage value. One example blockage value is the smallest cross-sectional area divided by the average cross-sectional area of all cross-sections.

The operating room controller 306 provides 614 the blockage value to the screen controller 312 and the screen controller 312 can receive the blockage value 616. For example, the screen controller 312 can instruct the screen 314 to present the blockage value in a GUI. Additionally or alternatively, the blockage value can be written to computer memory, transmitted to another computing device, or generate an alert for output to a user.

Figure 7:
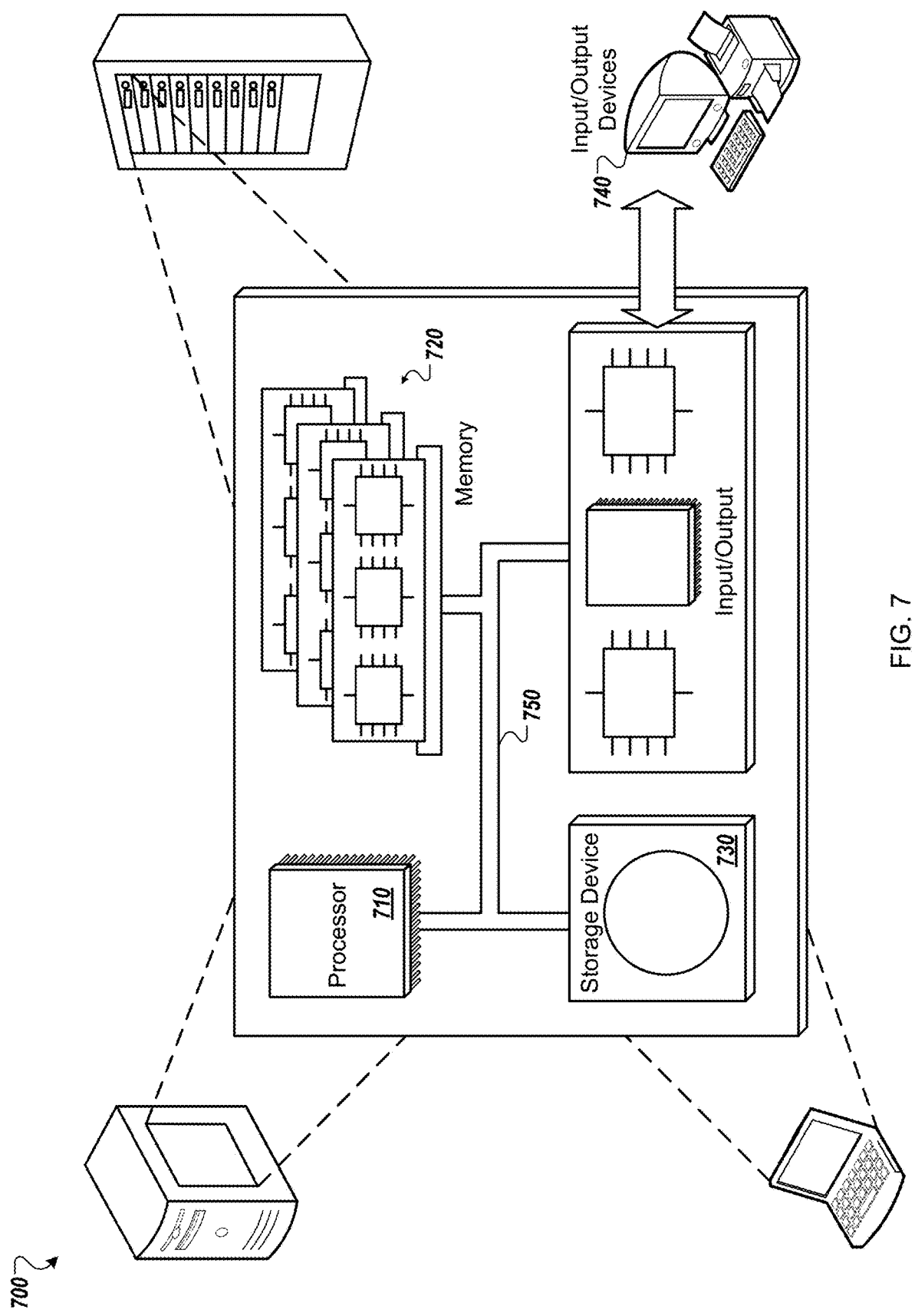
FIG. 7 is a block diagram of an example data processing apparatus.

FIG. 7 shows a block diagram of an example data processing apparatus 700 that can comprise the systems described herein. The system 700 includes a processor 710, a memory 720, a storage device 730, and an input/output device 740. Each of the components 710, 720, 730, and 740 can, for example, be interconnected using a system bus 750. The processor 710 is capable of processing instructions for execution within the system 700. In one implementation, the processor 710 is a single-threaded processor. In another implementation, the processor 710 is a multi-threaded processor. The processor 710 is capable of processing instructions stored in the memory 720 or on the storage device 730.

The memory 720 stores information within the system 700. In one implementation, the memory 720 is a computer-readable medium. In one implementation, the memory 720 is a volatile memory unit. In another implementation, the memory 720 is a non-volatile memory unit.

The storage device 730 is capable of providing mass storage for the system 700. In one implementation, the storage device 730 is a computer-readable medium. In various different implementations, the storage device 730 can, for example, include a hard disk device, an optical disk device, or some other large capacity storage device.

The input/output device 740 provides input/output operations for the system 700. In one implementation, the input/output device 740 can include one or more network interface devices, e.g., an Ethernet card, a serial communication device, e.g., an RS-232 port, and/or a wireless interface device, e.g., an 802.11 card. In another implementation, the input/output device can include driver devices configured to receive input data and send output data to other input/output devices, e.g., keyboard, printer and display devices 760. Other implementations, however, can also be used, such as mobile computing devices, mobile communication devices, set-top box television client devices, etc.

Embodiments of the subject matter and the operations described in this specification can be implemented in digital electronic circuitry, or in computer software, firmware, or hardware, including the structures disclosed in this specification and their structural equivalents, or in combinations of one or more of them. Embodiments of the subject matter described in this specification can be implemented as one or more computer programs, i.e., one or more modules of computer program instructions, encoded on computer storage medium for execution by, or to control the operation of, data processing apparatus.

A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially generated propagated signal. The computer storage medium can also be, or be included in, one or more separate physical components or media (e.g., multiple CDs, disks, or other storage devices).

The operations described in this specification can be implemented as operations performed by a data processing apparatus on data stored on one or more computer-readable storage devices or received from other sources.

The term "data processing apparatus" encompasses all kinds of apparatus, devices, and machines for processing data, including by way of example a programmable processor, a computer, a system on a chip, or multiple ones, or combinations, of the foregoing. The apparatus can include special purpose logic circuitry, e.g., an FPGA (field programmable gate array) or an ASIC (application specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., a FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few. Devices suitable for storing computer program instructions and data include all forms of non volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's user device in response to requests received from the web browser.

Embodiments of the subject matter described in this specification can be implemented in a computing system that includes a back end component, e.g., as a data server, or that includes a middleware component, e.g., an application server, or that includes a front end component, e.g., a user computer having a graphical user interface or a Web browser through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network ("LAN") and a wide area network ("WAN"), an internetwork (e.g., the Internet), and peer-to-peer networks (e.g., ad hoc peer-to-peer networks).

The computing system can include users and servers. A user and server are generally remote from each other and typically interact through a communication network. The relationship of user and server arises by virtue of computer programs running on the respective computers and having a user-server relationship to each other. In some embodiments, a server transmits data (e.g., an HTML page) to a user device (e.g., for purposes of displaying data to and receiving user input from a user interacting with the user device). Data generated at the user device (e.g., a result of the user interaction) can be received from the user device at the server.

Figure 8:
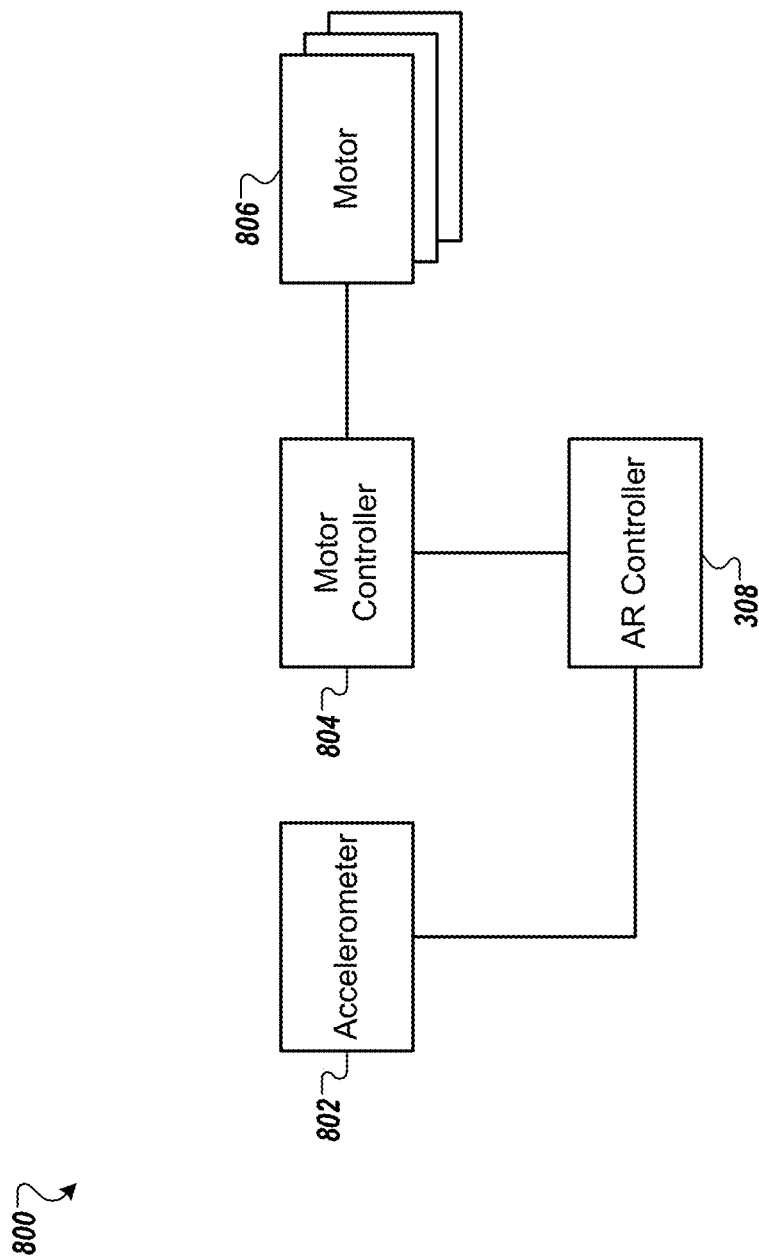
FIG. 8 shows a diagram of an example computing system that can be used for moving a shade of an augmented reality display.

FIG. 8 shows a diagram of an example computing system 800 that can be used for moving a shade member of an augmented reality display. For example, some embodiments of the augmented reality display 108 (FIG. 1A) can include an adjustable visor that is tinted. That is, the augmented reality display 108 can include a tinted adjustable visor can be selectively movable in relation to the other wearable portions of the augmented reality display 108. In some cases, this tinted visor can be used to render augmented reality elements in a way that is more visible than without a tinted visor (e.g., in comparison to an optically clear visor). However, the clinician 102 may not wish to have the tinted visor in place at all times. For example, the tinted visor may reduce visibility when observing real elements of the environment. To enable the augmented reality display 108 to have a computer-controllable, selectively movable tinted visor, the system 800 may be incorporated into, for example, the system 100.

An accelerometer 802 or multiple accelerometers are in data communication with the augmented reality controller 308. The accelerometer 802 may be integrally integrated with the augmented reality display 108, worn on a wristband, or otherwise worn on by the clinician 102. The accelerometer 802 may include elements that sense acceleration or other movement in one or more axes. These sensed accelerations can be transmitted to the augmented reality controller 308 (FIG. 3). This can allow the clinician 102 to provide gesture input to the system 800 via movement of their body where the accelerometer 802 is worn. Such a gesture input can be recognized by the system 800 as a command from the clinician 102 to actuate a movement of the tinted visor of the augmented reality display 108 (e.g., either to move the tinted visor into view or out of view of the clinician 102).

The augmented reality controller 308 can communicate with a motor controller 804 that controls one or more motors 806. The augmented reality controller 308 can issue commands to the motor controller 804 such as to lift the visor and lower the visor. The motor controller 804 can convert these logical instructions into motor instructions that drive the motors 806. The motors 806 may be connected to a hinge or sliding member of the visor, and may drive the visor into view and out of view of the clinician 102 in accordance with the command/instructions initiated by the clinician 102.

Figure 9:
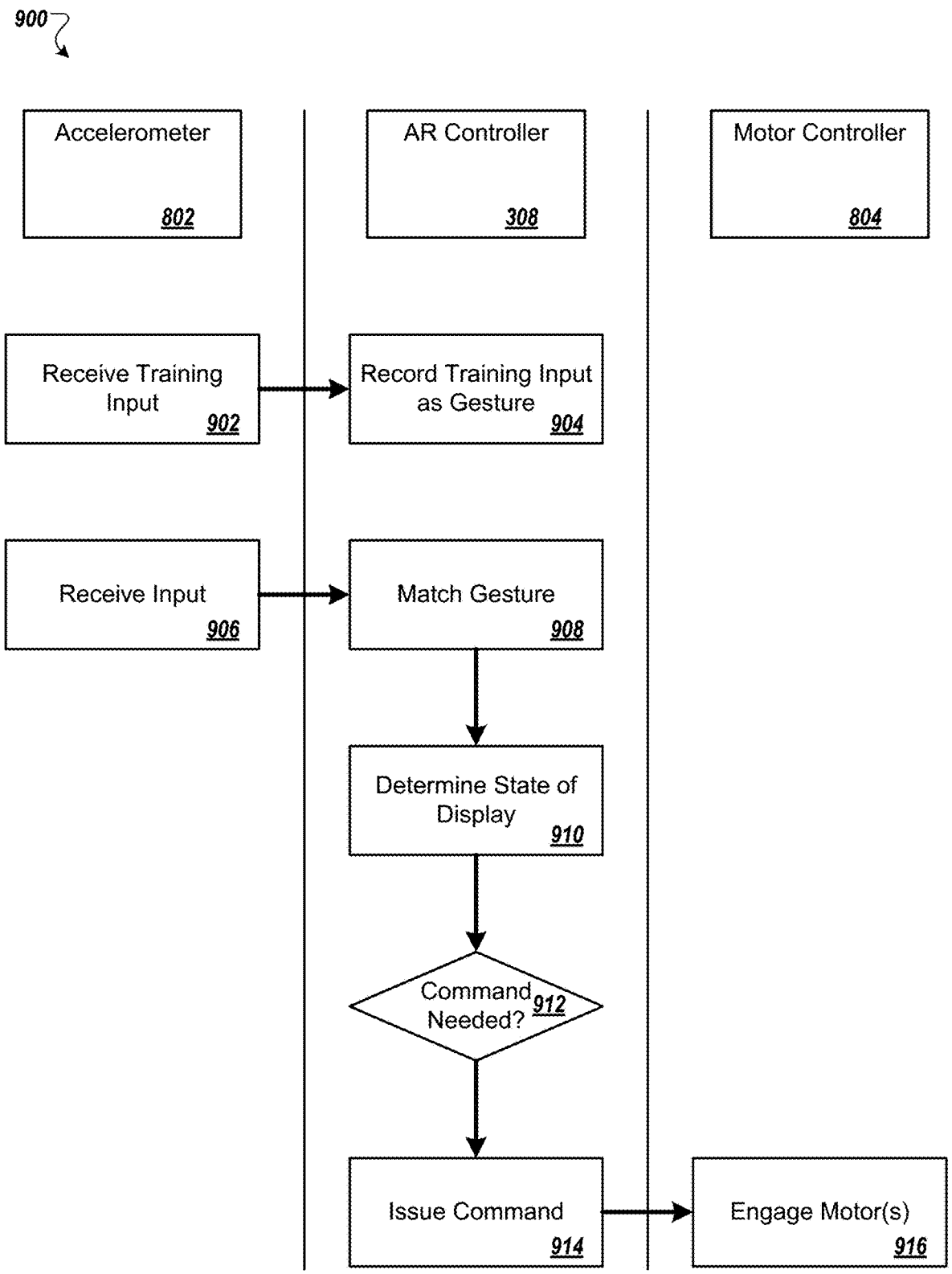
FIG. 9 shows a swimlane diagram of an example process that can be used for moving a shade of an augmented reality display.

FIG. 9 shows a swimlane diagram of an example process 900 that can be used for moving the visor of an augmented reality display. The process 900 may be used by, for example, the system 800 to raise and lower the tinted visor, but other systems may use the process 900 for similar or different uses.

The accelerometer 902 receives training input and the augmented reality controller 308 records the training input as a gesture 904. For example, the clinician 102 may put the system into a setup mode in which the clinician defines one or more gestures. As one example, the clinician 102 may flick their head upward to train a gesture to raise the visor and flick their head downward to train a gesture to lower the visor. Other head-based gestures include shaking the head or proscribing a circle with the clinician's 102 nose. In other embodiments, the accelerometer 802 may be mounted on a different part of the clinician's 102 body and different gestures may be used. For example, a foot-mounted accelerometer 802 may allow the clinician 1020 to gesture with their toes.

The movement of the accelerometer 802 creates a sequence of digital values recording the acceleration, and the accelerometer 802 can transmit these values to the augmented reality controller 308, which can store the values in memory along with the command the clinician would like to initiate with the gesture. In some cases, default gestures may be used in addition or instead.

The accelerometer receives input 906. When in use, the clinician 102 can execute the gesture with their body, creating input similar to the training gesture. The accelerometer can convert this input into acceleration values and provide the values to the augmented reality controller 308.

The augmented reality controller 308 can match the gesture input to a list of gesture inputs to determine if the gesture input represents an intention by the user to execute a visor movement command. As will be understood, non-gesture movements by the clinician 102 can create acceleration, and the augmented controller 308 can separate those readings from gesture input.

The augmented reality controller 308 can determine a state of the display 910. For example, a command to lower a visor that is already lowered may be ignored, or an error event may be thrown (e.g., a short beeping sound may be generated).

If the command is needed 912 based on the state of the display, the augmented reality controller 308 can issue the command 914.

The motor controller 904 can receive the command 916. For example, the motor controller 904 can convert the received commands into instructions to engage and disengage a motor at a particular speed, duration, number of steps, etc. In this way, the process 900 can cause the system 800 to be responsive to gesture input and to responsively move (e.g., pivot, slide, etc.) the visor in relation to other wearable portions of the augmented reality display 108 (and in relation to the clinician 102 who is wearing the augmented reality display 108).

Figure 10A:
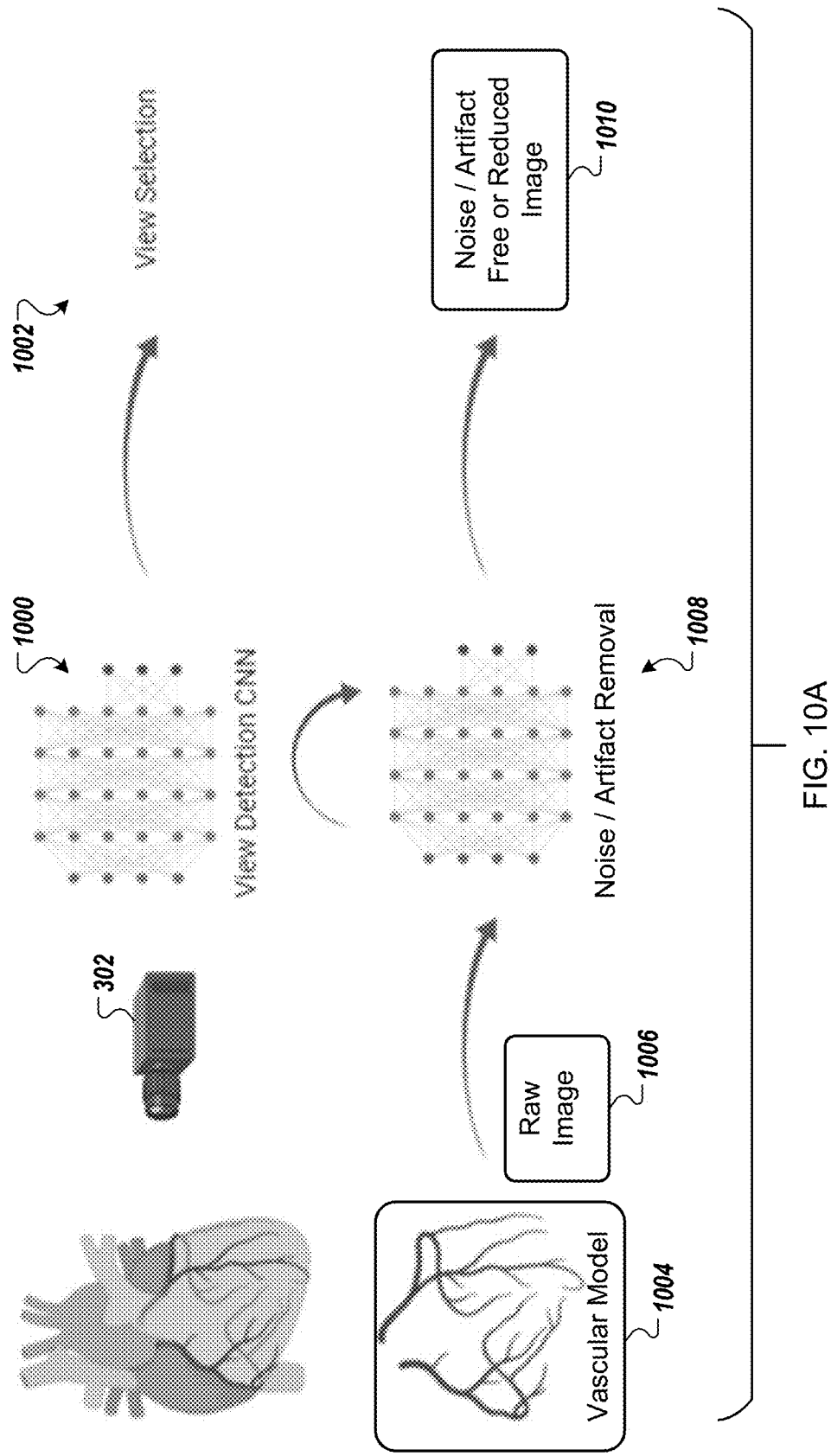
FIG. 10A shows a diagram of example data that can be used to remove artifacts from an augmented reality display.

FIG. 10A shows a diagram of example data that can be used to remove artifacts from an augmented reality display. Fluoroscopes 302 are often aligned to record data from a predefined set of possible orientations, which can produce standardized views of a patient 106. In order to determine which of the possible views is being presented, the operating room controller 306 (or another device) can submit the data from the fluoroscope 302 to a machine-learning system to categorize the data into one of the possible views.

For example, a convoluted neural network ("CNN") 1000 can be trained based on a training set of standard views from the fluoroscope 302 (FIG. 3) or other fluoroscopes. This CNN 1000 can receive a stream of data from the fluoroscope 302 and perform a number of operations to categorize 1002 the datastream into a view. This categorization 1002 may take the form of a single categorization (e.g., the name of the view selected), may be a single categorization with an associated confidence value to indicate the confidence of the selected categorization (e.g., with values near 1 indicating high confidence and values near 0 indicating low confidence), may take the form of multiple categorizations with each having an associated confidence value, or another format.

With a categorization 1002, a vascular model 1004 can be extracted. For example, a feature extraction operation can receive, as input, the raw images 1006 from the fluoroscope's 302 data stream and the categorization 1002 and perform image recognition operations to identify image features of vascular tissue. Then, these images may be used to generate a vascular model. In some cases, the vascular model is a collection of 2D pixels from the raw image 1006 identified as showing vascular tissue, and may be used, for example, as an image map. In another example, a 3D vascular model can be generated by fitting known-good 3D vascular shapes to constraints generated by the image recognition processes. Other vascular models may be used in other examples.

A noise/artifact removal CNN 1008 can be trained based on a training set of images that are free of noise and artifacts. For example, to create a training set, human users may access historically generated raw images 1006 and edit the images with image manipulation software to remove noise and artifacts. This may involve, for example, removal of stray black pixels (e.g., noise removal) and changing pixel values around wires and vascular tissue to more accurately represent the real shapes of these objects (e.g., artifact removal). In one example, a wire may pass under vascular tissue in a training image. Such an arrangement in this example results in an artifact showing a thinning of the wire, and in this example the user may edit some of the white pixels to the black value to remove the artifact. Further, the CNN 1008 may record constraints on shapes that should be or must be honored by the noise/artifact removal process. For example, as wires and vascular tissue often have smooth edges, an edge-smoothness constraint may be operationally recorded in the CNN 1008 to enforce edits to conform to this edge smoothness.

With a vascular model 1004 and a raw image 1006, the CNN 1008 can produce an image 1010 that is free of, or has reduced, image artifacts and/or noise. An example of a raw image 1006 and image 1010 is shown in FIG. 10B.

The raw image 1006 contains an artifact 1050, where vascular tissue is not shown in black. In image 1010, this artifact 1050 has been reduced or eliminated, properly showing the phenomena being imaged.

The raw image 1006 contains noise 1052, where non-vascular tissue, or more precisely non-contrasted tissue, is shown in black. In image 1010, this noise 1052 has been reduced or eliminated, properly showing the phenomena being imaged.

The raw image 1006 contains an artifact 1054, where vascular tissue is not shown in black and is shown with insufficient smoothness. In image 1010, this artifact 1054 has been reduced or eliminated and the edges of the vascular tissue have been smoothed, properly showing the phenomena being imaged.

The raw image 1006 contains an artifact 1056, where portions of a wire are shown with insufficient smoothness. In image 1010, this artifact 1056 has been corrected by modifying the edges of the wire having been smoothed, properly showing the phenomena being imaged.

Figure 11:
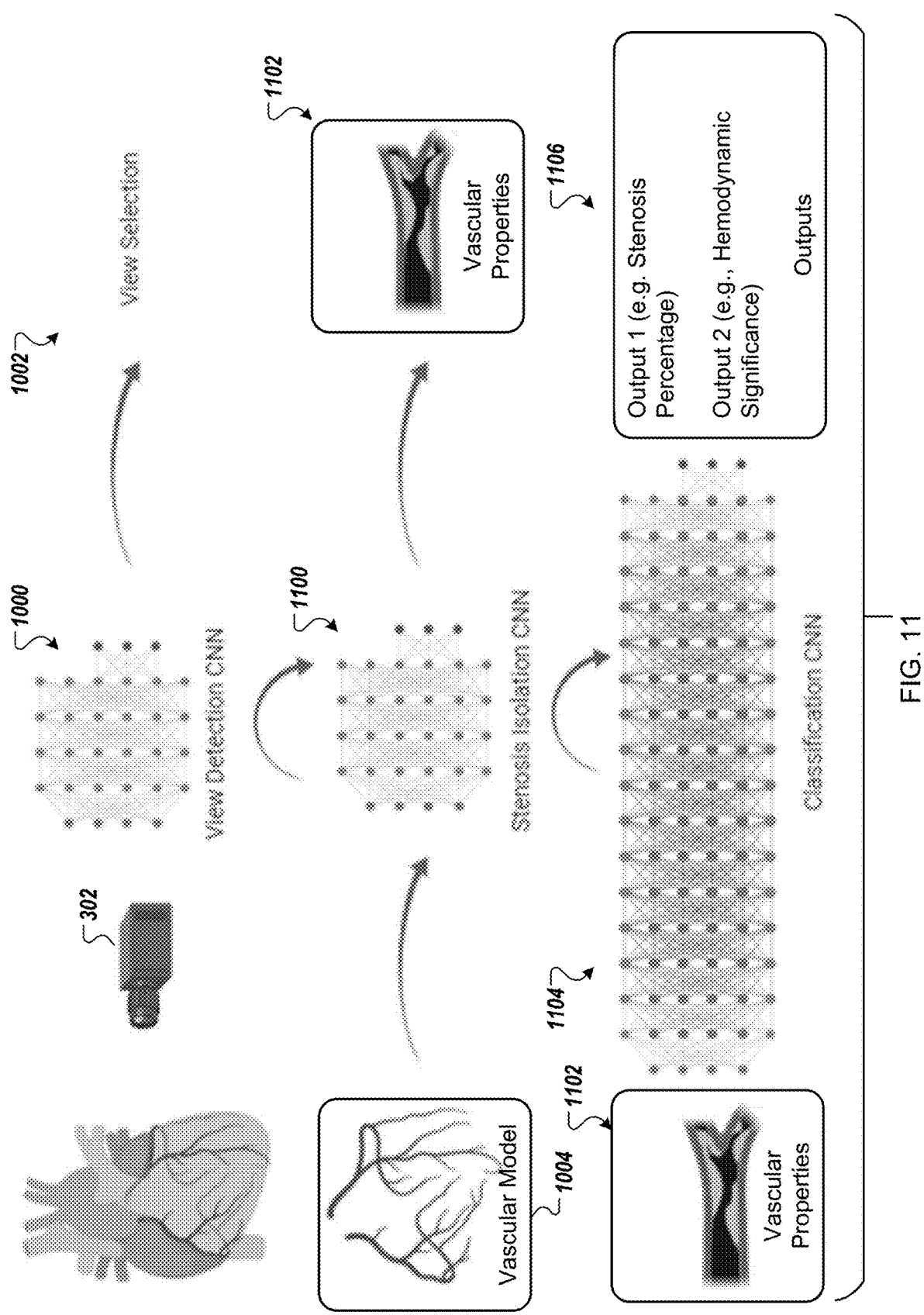
FIG. 11 shows a diagram of example data that can be used to classify vascular tissue.

FIG. 11 shows a diagram of example data that can be used to classify vascular tissue. For example, vascular tissue can be classified with clinically relevant data that can be displayed to the clinician 102 while the clinician 102 is viewing the noise/artifact reduced or free video of the patient 106.

A stenosis isolation CNN 110 can be trained based on a training set of clinically tagged vascular models in the same format as the vascular model 1004. For example, one clinician or multiple clinicians may each visually examine a rendering of the training models and enter a topological definition that defines a shape of a stenosis of each rendering, possibly with confidence values to represent their confidence in the accuracy of the diagnosis. These topologies and confidence values may be used as isolations of stenoses and confidence values to train the CNN 1100.

To determine the vascular properties 1102 The CNN 1100 can receive a vascular model 1004 of the patient 106 and perform a number of operations to categorize 1102 the vascular model into a collection of one or more categories. This categorization 1102 may take the form of a single categorization (e.g., a topological definition that defines a shape), may be a single categorization with an associated confidence value to indicate the confidence of the selected categorization (e.g., with values near 1 indicating high confidence and values near 0 indicating low confidence), may take the form of multiple categorizations with each having an associated confidence value, or another format. As will be understood, other categorizations may be used, including but not limited to clinical diagnoses and subclinical diagnoses.

A classification CNN 1104 can be trained on a training set of topologies of the type previously described. For example, to create a training set, human users may classify the stenoses of the training set of the CNN 1100, of different stenoses, or of both different stenoses and the stenoses of the training set of the CNN 1100. In another example that may be used alone or in combination with the human analysis, fluid-dynamic or other computational analyses may be performed on the training set to produce result values. These inputs (stenoses topologies) and outputs (human or computational classifications) may or may not include confidence values, and may be used to train the CNN 1104.

With the vascular properties 1102, the CNN 1004 can produce stenoses classifications 1106. In one example, the outputs 1106 include a stenosis percentage and a probability of hemodynamic significance. In some examples, the one or more outputs may have confidence values associated, and in some examples, more, fewer, and other outputs may be used.

Figure 12A:
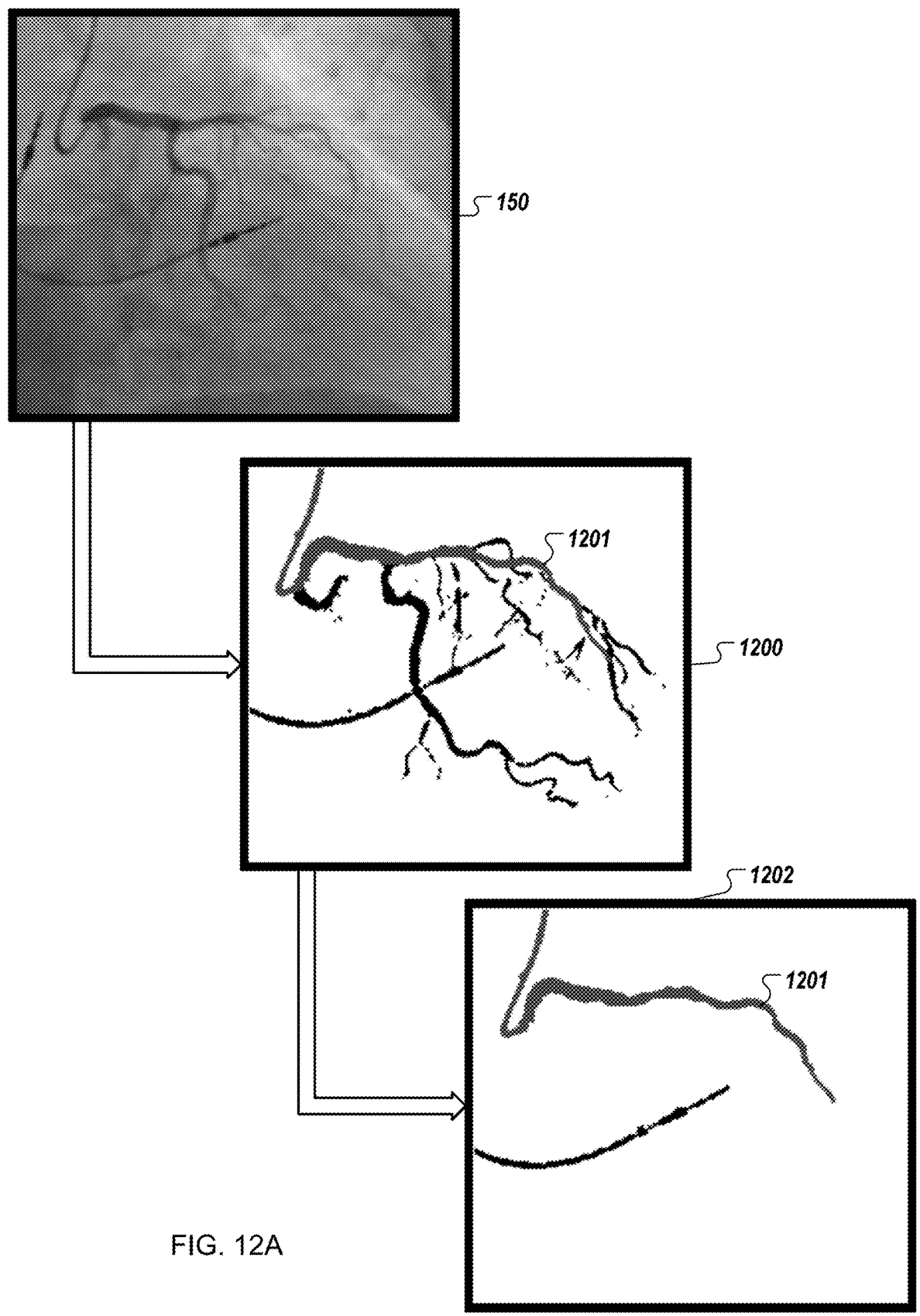
FIGS. 12A and 12B show examples of images presented in augmented reality with roadmap overlays.
Figure 12B:
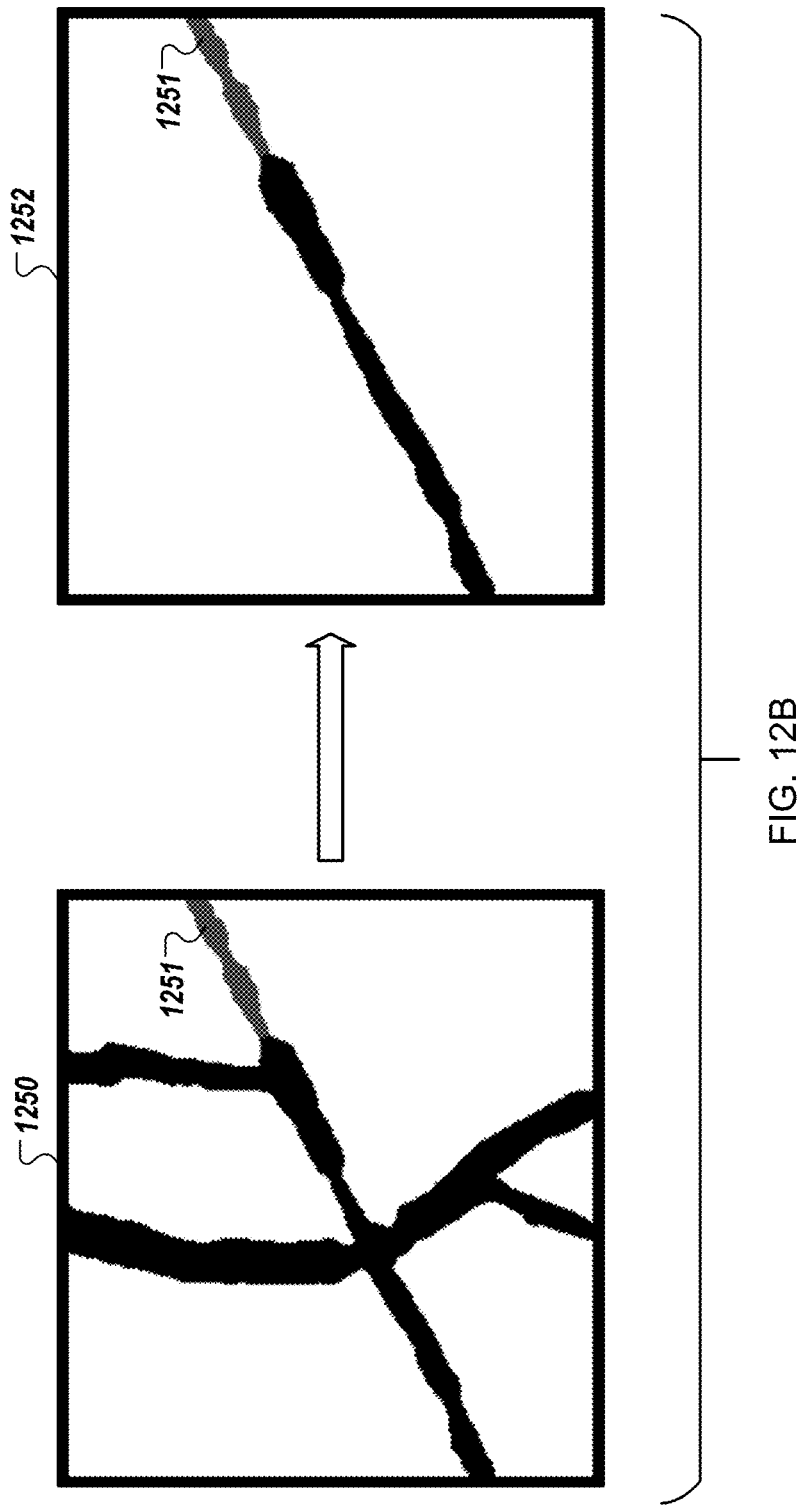

FIGS. 12A and 12B show examples of images presented in augmented reality with roadmap overlays. In some cases, a roadmap overlay can be applied to augmented reality images to aid the clinician 102. The roadmap may advantageously provide information in the augmented reality display to help the clinician guide a wire even when the surrounding vascular tissue does not have enough contrast dye to make visible the vascular tissue via the fluoroscope 104.

The clinician 102, or an automated system such as the CNN 1000, can specify a roadmap in the vascular model 1004 for a given procedure. This roadmap may include a definition of a travel-path for an instrument through vascular tissue. In some cases, this definition may include a 3D path through a 3D model of vascular tissue. In some cases, this definition may include a 2D path through a 2D model of vascular tissue.

The operating room controller 306 can generate augmented-reality display elements to show the travel-path. For example, when generating the high-contrast videostream 508, the operating room controller can further render the travel-path as a graphical element to be overlaid over the elements representing vascular tissue.

Because vascular tissue is often stationary or nearly-stationary during many procedures, the travel-path can be oriented at the beginning of the procedure, when the vascular tissue houses enough contrast dye to be easily visible by a human operator, automated image-recognition process, or semi-automated image-recognition process.

Once oriented, the travel-path can be rendered in a way that allows it to be seen in the augmented-reality. In FIG. 12A, the image 150 is the greyscale image created by the medical imager 104. Image 1200 is created as previously described, and by applying a red mask 1201 over the travel-path area. Other displays of the travel path are possible, including dynamic information (e.g., blinking elements), textured masks, 3D renders in 2D that preserve shadow and highlight to show volume, and user-adjustable graphical properties.

Later, as the contrast dye is diluted, the vascular tissue fades from the image 105 and thus the image 1200. As will be understood, metal and other radiopaque materials are still shown with high contrast. In 1202, the travel-path 1201 is displayed even as the vascular tissue is no longer radiopaque and thus not visible. With such a display, the clinician 102 can advantageously continue to perform the procedure without use of, or with less use of, contrast dye.

In FIG. 12B, a noise/artifact free or reduced image 1250 is shown with a travel-path 1251. Later, as contrast dye is diluted and the vascular tissue is no longer visible, the travel-path 1251 is still visible. As will be understood, the travel-path can be displayed over high-contrast images that do or do not have noise/artifact reduction techniques applied.

While this specification contains many specific implementation details, these should not be construed as limitations on the scope of any inventions or of what may be claimed, but rather as descriptions of features specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described herein should not be understood as requiring such separation in all embodiments, and it should be understood that the described program components and systems can generally be integrated together in a single product or packaged into multiple products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

What is claimed is:

1. A system, comprising:
   a head-worn display comprising a view-area and a renderer configured to render onto the view-area;
   a central controller comprising a processor and memory;
   an augmented-reality controller comprising a processor and memory;
   an imaging sensor comprising a radiation sensor, the imaging sensor configured to sense phenomena in a patient's body based on a reception of radiation that has passed through the patient's body; and
   an imaging controller comprising a processor and memory, the imaging controller configured to: (i) generate an imaging-datastream formatted to contain gradient data having at least one range of values based on the sensed phenomena and (ii) transmit, to the central controller, the imaging-datastream,
   wherein the central controller is configured and programmed to:
      receive the imaging-datastream;
      automatically generate, from the imaging-datastream, a high-contrast videostream comprising monochromatic data having a selected value from a plurality of specified values by automatically converting the gradient data to the monochromatic data, wherein surgical tools and vascular tissue are represented with a dark monochromatic color corresponding to a first value of the plurality of specified values and surrounding non-vasculature tissue is represented with a light monochromatic color corresponding to a second value of the plurality of specified values, the dark monochromatic color being darker than the light monochromatic color; and
      transmit, to the augmented-reality controller, the high-contrast videostream,
   wherein the augmented-reality controller is configured to: (i) receive the high-contrast videostream and (ii) instruct the head-worn display to render the high-contrast videostream such that the surgical tools and the vascular tissue are rendered with the dark monochromatic color, and
   wherein the head-worn display is configured to display the high-contrast videostream such that: i) the surgical tools and the vascular tissue are rendered onto the view-area in the dark monochromatic color and ii) the surrounding non-vasculature tissue is rendered onto the view-area in the light monochromatic color, and
   wherein the light monochromatic color is transparent such that images of environments beyond the head-worn display transmit through the light monochromatic color to be visible by a wearer of the head-worn display.

2. The system of claim 1, wherein to generate, from the imaging-datastream, the high-contrast videostream in which surgical tools and vascular tissue is represented with a dark monochromatic color, the central controller is further configured to:
   generate, from the imaging-datastream, a full-scale videostream in which surgical tools and vascular tissue have a first contrast with surrounding tissue; and
   generate, from the full-scale videostream, the high-contrast videostream such that in the high-contrast videostream, surgical tools and vascular tissue have a second contrast with surrounding tissue, the second contrast being greater than the first contrast.

3. The system of claim 2, wherein to generate, from the full-scale videostream, the high-contrast videostream, the central controller is further configured to increase the contrast of the full-scale videostream such that the high-contrast videostream contains only the dark monochromatic color and the light monochromatic color.

4. The system of claim 2, wherein to generate, from the full-scale videostream, the high-contrast videostream, the central controller is further configured to invert the colors of the full-scale videostream.

5. The system of claim 1, wherein the augmented-reality controller is communicably coupled to the head-worn display by at least a data cable;
   the system further comprising a sterile gown having a port through which the data cable can pass, resulting in the augmented-reality controller being wearable by a wearer in a sterile environment and the augmented-reality controller being wearable by the wearer in a non-sterile environment.

6. The system of claim 1, wherein the head-worn display comprises radiation shielding positioned to protect a wearer from radiation.

7. The system of claim 1, wherein the central controller is further configured to determine a measure of blockage of an area of vascular tissue.

8. The system of claim 1, wherein the central controller is further configured to:
   receive a gesture input supplied by a wearer of the head-worn display;
   issue at least one command to a position of a visor of the head-worn display.

9. The system of claim 1, wherein the central controller uses at least one neural network to reduce or eliminate, from the high-contrast videostream, at least one of the group consisting of 1) noise; and 2) an artifact.

10. The system of claim 1, wherein the central controller uses at least one neural network to automatically generate at least one classification of a stenosis.

11. The system of claim 1, wherein the central controller augments the high-contrast videostream with a travel-path element using a third color that is different than the dark monochromatic color and different than the light monochromatic color.

12. A central controller comprising a processor and memory, the central controller configured and programmed to:
   receive an imaging-datastream from an imaging controller, the imaging controller configured to (i) generate the imaging-datastream formatted to contain gradient data having at least one range of values gradient data based on a sensed phenomena and (ii) transmit, to a central controller, the imaging-datastream;
   automatically generate, from the imaging-datastream, a high-contrast videostream comprising monochromatic data having a selected value from a plurality of specified values by automatically converting the gradient data to the monochromatic data, wherein surgical tools and vascular tissue are represented with a dark monochromatic color corresponding to a first value of the plurality of specified values and surrounding non-vascular tissue is represented with a light monochromatic color corresponding to a second value of the plurality of specified values, the dark monochromatic color being darker than the light monochromatic color; and transmit, to an augmented-reality controller, the high-contrast videostream such that a head-worn display coupled to the augmented-reality controller is capable of displaying the high-contrast videostream such that i) the surgical tools and the vascular tissue are rendered onto a view-area of the head-worn display in the dark monochromatic color and ii) the surrounding non-vascular tissue is rendered onto the view-area in the light monochromatic color, and wherein the light monochromatic color is transparent such that images of environments beyond the head-worn display transmit through the light monochromatic color to be visible by a wearer of the head-worn display.

13. The central controller of claim 12, wherein to generate, from the imaging-datastream, the high-contrast videostream in which surgical tools and vascular tissue is represented with a dark monochromatic color, the controller is further configured to:

generate, from the imaging-datastream, a full-scale videostream in which surgical tools and vascular tissue have a first contrast with surrounding tissue; and generate, from the full-scale videostream, the high-contrast videostream such that in the high-contrast videostream, surgical tools and vascular tissue have a second contrast with surrounding tissue, the second contrast being greater than the first contrast.

14. The central controller of claim 13, wherein to generate, from the full-scale videostream, the high-contrast videostream, the central controller is further configured to increase the contrast of the full-scale videostream such that the high-contrast videostream contains only the dark monochromatic color and the light monochromatic color.

15. The central controller of claim 13, wherein to generate, from the full-scale videostream, the high-contrast videostream, the central controller is further configured to invert the colors of the full-scale videostream.

16. The central controller of claim 12, wherein the central controller is further configured to determine a measure of blockage of an area of vascular tissue.

17. The central controller of claim 12, wherein the central controller is further configured to:

receive a gesture input supplied by a wearer of a head-worn display;

issue at least one command to a position of a visor of the head-worn display.

18. The central controller of claim 12, wherein the central controller uses at least one neural network to automatically generate at least one classification of a stenosis.

19. The central controller of claim 12, wherein the central controller augments the high-contrast videostream with a travel-path element using a third color that is different than the dark monochromatic color and different than the light monochromatic color.

20. A non-transitory computer-readable medium comprising instructions that, when executed, cause a controller to be programmed to:

receive an imaging-datastream from an imaging controller, the imaging controller configured to (i) generate the imaging-datastream formatted to contain gradient data having at least one range of values gradient data based on a sensed phenomena and (ii) transmit, to a central controller, the imaging-datastream;

automatically generate, from the imaging-datastream, a high-contrast videostream comprising monochromatic data having a selected value from a plurality of specified values by automatically converting the gradient data to the monochromatic data, wherein surgical tools and vascular tissue are represented with a dark monochromatic color corresponding to a first value of the plurality of specified values and surrounding non-vasculature tissue is represented with a light monochromatic color corresponding to a second value of the plurality of specified values, the dark monochromatic color being darker than the light monochromatic color; and transmit, to an augmented-reality controller, the high-contrast videostream such that a head-worn display coupled to the augmented-reality controller is capable of displaying the high-contrast videostream such that i) the surgical tools and the vascular tissue are rendered onto a view-area of the head-worn display in the dark monochromatic color and ii) the surrounding non-vasculature tissue is rendered onto the view-area in the light monochromatic color, and wherein the light monochromatic color is transparent such that images of environments beyond the head-worn display transmit through the light monochromatic color to be visible by a wearer of the head-worn display.

* * * * *